United States Patent [19]

Sabol

[11] 4,031,017

[45] June 21, 1977

[54] PHOSPHOSULFURIZED HYDROCARBON MODIFIED N-(HYDROXY AND ALKYL-SUBSTITUTED BENZYL) ALKYLENE POLYAMINE

[75] Inventor: Albert R. Sabol, Munster, Ind.

[73] Assignee: Standard Oil Company (Indiana), Chicago, Ill.

[22] Filed: Apr. 7, 1976

[21] Appl. No.: 674,614

[52] U.S. Cl. .............................. 252/46.7; 252/47.5; 260/125; 260/136; 260/981
[51] Int. Cl.$^2$ ......................................... C09B 49/00
[58] Field of Search ....................... 252/46.7, 47.5; 260/125, 136

[56] References Cited

UNITED STATES PATENTS

| | | | |
|---|---|---|---|
| 3,368,972 | 2/1968 | Otto | 252/47.5 |
| 3,458,495 | 7/1969 | Younghouse | 260/136 |
| 3,957,746 | 5/1976 | Malec | 252/46.7 |
| 3,985,802 | 10/1976 | Piasek et al. | 252/47.5 |

*Primary Examiner*—Arthur P. Demers

*Attorney, Agent, or Firm*—Fred R. Ahlers; Arthur G. Gilkes; William T. McClain

[57] ABSTRACT

This invention relates to a novel lubricant oil addition agent which is a phosphosulfurized $C_{35}$ to $C_{160}$ hydrocarbon modified N-(hydroxy and $C_{50} - C_{160}$ alkyl-substituted benzyl) alkylene polyamine. Such novel addition agent imparts anti-oxidant and unexpected dispersancy functions to lubricant oils commonly used as crankcase lubricants for internal combustion engines. Such novel addition agent also imparts anti-oxidant and detergency functions to the less viscous oils used to lubricate automatic transmissions and at the same time prevent failure of the rubber seals used therein from deterioration (hardening) by oxidation and distortion softening by undue swelling. The present inventive addition agent unexpectedly provides both detergency and an anti-oxidant functions for lubricant oil which are superior to the related analog addition agent derived from the reaction of one molar proportion of a phosphosulfurized 500 to 2800 (Staudinger) molecular weight hydrocarbon with from 0.5 up to 4 molar proportion of an N-(hydroxy and $C_4 - C_{24}$ alkyl-substituted benzyl) alkylene polyamine.

6 Claims, No Drawings

PHOSPHOSULFURIZED HYDROCARBON MODIFIED N-(HYDROXY AND ALKYL-SUBSTITUTED BENZYL) ALKYLENE POLYAMINE

BACKGROUND OF THE INVENTION

The N-(hydroxy and $C_4 - C_{24}$ alkyl-substituted benzyl) alkylene polyamines of the class $H_2N-(R-NH)_nH$, wherein R, is a $C_2$ to $C_6$ alkylene hydrocarbon radical and $n$ is an integer of from 1 up to 10 have been long known. Such N-substituted alkylene polyamines are derived from the condensation of a $C_4 - C_{24}$ alkylphenol, a source of formaldehyde and an alkylene polyamine of the above formula. Those skilled in the art of formulating crankcase lubricant compositions know that the above long known N-substituted alkylene polyamines impart little or no significant detergency function to oils use to lubricate the internal moving parts of internal combustion engines in use since the advent in 1960 of increasingly severe restrictions on gas and vapor emission from the engines crankcase.

Such detergency deficient N-(hydroxy and $C_4 - C_{24}$ alkyl-substituted benzyl) alkylene polyamines were improved with respect to detergency by their modification, according to U.S. Pat. No. 3,458,495, with a phosphosulfurized 500 to 200,000 (Staudinger) molecular weight hydrocarbon which could be a terpene, a heavy petroleum fraction or a polymer of a $C_2$ to $C_6$ olefin. The improved addition agent of said patent is obtained by reacting at a temperature of from 93° up to 232° C one molar proportion of such phosphosulfurized hydrocarbon with from 0.5 up to 4 molar proportions of the N-(hydroxy and $C_4 - C_{24}$ alkyl-substituted benzyl) alkylene polyamines.

The above phosphosulfurized modified N-(hydroxy and $C_4 - C_{24}$ alkyl-substituted benzyl) alkylene polyamines are recognized as representing prior art knowledge closest to the present inventive addition agents. Such close prior addition agents are, as will be later demonstrated, deficient with respect to detergency-dispersancy requirements of present day internal combustion engines which have been required to have a substantially closed system coupling the vapor space of the crankcase and combustion chambers of the engines so that there is no venting of the crankcase to the atmosphere. Such a closed, coupled system by recycle of combustion products passing by the piston rings to the crankcase and lubricant oil decomposition products cause the formation of oil-insoluble sludges which are more difficult to disperse in the lubricating oil. Also the closed, coupled system materially enhances partial oxidation of petroleum derived lubricating oils causing them to have a four-fold increase in viscosity in a relatively short time, about 20–35 hours of engine operation.

Although the closest prior art addition agents of U.S. Pat. No. 3,458,495 were suitable detergents at the time of their discovery and disclosure in 1965, it is understandable that they are now detergency and dispersancy deficient more than ten years later because of the above-mentioned more severe service imposed by the required use of the closed, coupled system between the crankcase and combustion portions of the internal combustion engines.

Another drawback of said closest prior art addition agents comes from the use of phosphosulfurized hydrocarbons of a molecular weight above 2800 which corresponds to a carbon content in the molecule of above 200. Such hydrocarbons of molecular weight above 2800, and especially the olefin polymers, vary from extremely viscous liquids to semisolids at ambient temperature. For example, at a molecular weight of about 3000 such hydrocarbons will have a viscosity above 200,000 centistokes at 37.5° C and above 6000 at 98.5° C. After conversion of such 2800 and high molecular weight hydrocarbons with a phosphorus sulfide to the phosphosulfurized derivative, the phosphosulfurized hydrocarbon product not only retains the exceptionally high viscosity of its hydrocarbon precursor but also has a higher viscosity. The use of phosphosulfurized hydrocarbons of greater than 200 carbon content to modify the N-(hydroxy and alkyl-substituted benzyl) alkylene polyamines leads to addition agents which at conventional use in lubricating oil, from 0.1 up to 10 weight percent of the oil, would provide a lubricant oil composition of undesirably high viscosity at temperatures from ambient up to engine operating temperatures.

For the beneficial use of the present inventive addition agents, it is not necessary to use a phosphosulfurized hydrocarbon derived from a hydrocarbon of molecular weight above 2800. Rather such phosphosulfurized hydrocarbon reactant is one which has been obtained by the reaction of a phosphorus sulfide, preferably phosphorus pentasulfide, with an olefin polymer of number average molecular weight ($\overline{M}_n$) in the range of from 500 up to 2600, preferably from 700 up to 2240. Such olefin polymers have a number average carbon ($\overline{C}_n$) content of from about 35 up to about 186, preferably from 50 to about 160 $\overline{C}_n$.

However, the present inventive addition agent differs more than in the foregoing basis for selection of the phosphosulfurized hydrocarbon reactant. While such selection provides part of the novelty for the present inventive addition agent, the remaining portion of the novelty comes from the selection of the N-(hydroxy and alkyl-substituted benzyl) alkylene polyamine reactant. For the selection of such N-substituted alkylene polyamines, it is the selection of its alkyl-substituted phenol precursor that is believed to be of importance with respect to the above-mentioned remaining novelty. For such N-substituted alkylene polyamine reactant the alkylphenol reactant of importance has an alkyl-substituent derived from an olefin polymer having a carbon content of from about 50 up to about 160 which corresponds to a 700 up to 2240 $\overline{M}_n$. The upper limit on the size of such olefin polymer derived alkyl-substituted is also related to the viscosity characteristics of the olefin polymer which is used to alkylate phenol to obtain the alkylphenol precursor of the N-substituted alkylene polyamine portion of the present inventive addition agent.

The same viscosity-molecular weight correlation discussed with respect to the phosphosulfurized hydrocarbon reactant are applicable to the correlations between viscosity-molecular weight of the olefin polymer which also carry through to both the alkylphenol precursor and the N-substituted alkylene polyamine. But such selection of alkylphenol precursor of the N-substituted alkylene polyamine is of further importance to the unexpected dispersancy function of the present inventive addition agent.

It is the combination of the technical effects of the selected phosphosulfurized 500–2600 $M_n$ hydrocarbon and the selected N-(hydroxy and alkyl-substituted benzyl) alkylene polyamine reactants and the proportions of such reactants later given which provide the novelty for the present inventive addition agent which imparts anti-oxidant, detergency and unexpectedly superior dispersancy functions to lubricant oil fractions of petroleum.

The closest prior art phosphosulfurized hydrocarbon modified N-(hydroxy and alkyl-substituted benzyl) alkylene polyamines are disclosed as being produced in three steps. The phosphosulfurized hydrocarbon reactant is separately prepared The second step comprises the condensation of the $C_4 - C_{24}$ alkylphenol, a source of formaldehyde (e.g. formalin or paraformaldehyde) and alkylene polyamine. In the last step one molar proportion of the phosphosulfurized hydrocarbon is reacted at a temperature of from 93° up to 232° C with from 0.5 up to 4 molar proportions of the N-(hydroxy and $C_4 - C_{24}$ alkyl-substituted benzyl) alkylene polyamine condensation product of the second step. While products analagous to the present inventive addition agent can be produced by the same three reaction steps, the present inventive addition agent is preferably produced by only the following two reaction steps. The phosphosulfurized olefin polymer is separately prepared and then combined with the $C_{50} - C_{160}$ alkylphenol and the alkylene polyamine followed by addition of a source of formaldehyde to the three combined reactants to complete the production of the present inventive addition agent for lubricant oil fraction of petroleum.

Such preferred two step reaction is, from the following considerations, novel in view of the three step prior process for producing the closest prior art addition agents. It is known that the phosphosulfurized olefin polymer is acidic in nature and will readily react with an alkylene polyamine. Such reaction does in fact occur in the second step of the preferred two step reaction. the character and nature of such reaction is not known and not important to the present invention except that the product of such reaction does have at least one hydrogen on a nitrogen atom in the reaction producct to undergo a condensation reaction with formaldehyde and the alkylphenol and split out water as a by-product.

Because one molar proportion of the phosphosulfurized olefin polymer hydrocarbon can be reacted with less than, more than and equal molar proportions of each of the $C_{50} - C_{160}$ alkylphenol alkylene polyamine and formaldehyde, the present inventive addition agent resulting therefrom can not be characterized in the normal manner, i.e. by structural formula. Moreover, both the phosphosulfurized hydrocarbon and alkylphenol reactants are derived from olefin polymers which even when designated by a single $\overline{M}_n$, e.g. 900 $\overline{M}_n$, are not single molecular entities but rather are mixtures of higher and lower molecular weight species. This further prevents characterization of the present inventive addition agent in a normal manner for identifying organic chemical compounds.

The character and nature of the phosphosulfurized olefin polymer is further complex with respect to its phosphorus and sulfur linkages carrying through from the phosphorus sulfide reactant. There is definitely a quite stabile carbon-to-phosphorus linkage but there are both coordinate and polar linkages between the phosphorus and sulfur atoms. The preferred phosphosulfurized olefin polymer obtained from phosphorus pentasulfide can have carbon-to-sulfur, carbon-to-phosphorus, mono-and di-coordinate linkages between phosphorus and sulfur and polar linkages between phosphorus and sulfur as in the following structure from one mole of $P_2S_5$ and two moles of olefin polymer:

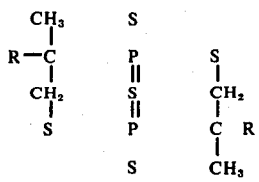

Such a complex molecule has many potential routes for reaction with an alkylene polyamine.

Because of the foregoing complexities associated with the preparation and formation of the present inventive addition agent, it can be only defined as a reaction product in terms of its reactants, their molar proportions, and reaction conditions.

STATEMENT OF INVENTION

The present inventive lubricant oil addition agent is the reaction product obtained from 1.0 molecular proportion of $C_{50}$ to $C_{160}$ alkyl-substituted phenol, from 0.1 up to 10 molecular proportions of alkylene polyamine, from 1.0 up to 10 molecular proportions of formaldehyde, and from 0.1 up to 10 molecular proportions of phosphosulfurized olefin polymer of from 500 up to 2240 $\overline{M}_n$. The preferred inventive addition agent is obtained from 1.0 molecular proportion of $C_{50}$ to $C_{160}$ alkyl-substituted phenol, from 0.5 up to 2.0 molecular proportions of alkylene polyamine, from 1.5 up to 4 molecular proportions of formaldehyde, and from 0.5 up to 3.0 molecular proportions of the phosphosulfurized hydrocarbon from the reaction of a 500 up to 1120 $M_n$ olefin polymer having a viscosity at 98.5° C of from 60 up to 640 with one mole $P_2S_5$.

Such addition agent is produced from said reactants and their molecular proportions under condensation reaction conditions which split out and remove water. Suitable condensation reaction condtions are from 70° C up to 180° C. The reaction or reactions can be conducted in a reaction diluent such as benzene, toluene, xylene or an olefin-free petroleum fraction of the lubricant oil range. Such lubricant oils range from SAE-5W oil (viscosities of 4000 Saybolt Seconds maximum at −18° C and 39 Saybolt Seconds minimum at 98.5° C) up to SAE-30 oil (viscosity in the range of 58 to 70 Saybolt Seconds at 98.5° C). When the addition agent is prepared in the aromatic hydrocarbon diluent, all the water byproduct of the condensation reaction can be removed as an azcotropic mixture with vaporized aromatic hydrocarbon. By continuing the distillative removal of the aromatic hydrocarbon until it has been completely removed, the residual material is the oil-soluble addition agent. Thereafter, for convenience in formulating the lubricant oil composition containing the present inventive addition agent such distillation residue can be taken up in an amount of lubricant oil of the SAE-5W to SAE-30 classification range to obtain a 10 to 50 weight percent concentration of the addition agent.

Such an oil solution concentrate of the present inventive addition agent can also be prepared by conducting the reactions of the above designated reactants in the lubricant oils of the SAE-5W to SAE-30 classification. Removal of by-product water at the 70° to 180° C temperature range can be accomplished at subatmospheric pressure at temperatures of 70° to 100° C and at atmospheric pressure. In either case, the water removal can be aided by injecting inert gas (e.g. nitrogen or carbon dioxide) into the heated reaction mixture.

Removal of by-product water from the reaction conducted in the aromtic hydrocarbon or lubricant oil reaction diluent also removes hydrogen sulfide generated by the reaction of phosphosulfurized hydrocarbon with an amino group of the alkylene polyamine or its residual group in the N-(hydroxy and alkyl-substituted benzyl) alkylene polyamine preformed for reaction with the phosphorsulfurized olefin reactant.

EMBODIMENTS OF THE INVENTION

Representative addition agent products contemplated within the present invention can be prepared from the following representative reactants of the classes of reactants before defined.

1. Alkyl-Substituted Phenol

Representative of such alkylphenol reactants are those having an alkyl hydrocarbon substituent of from 50 up to 160 carbon atoms. Such alkylphenols can be prepared by the alkylation of phenol with the appropriate carbon content mono-olefin. One convenient method for such alkylation of phenol is described in British Patent Specification No. 1,159,368. Said patent describes the alkylation of phenol with an olefin polymer in the presence of a $BF_3$ phenolate catalyst. Such catalysis when used with butene polymers, causes some molecular weight degradation of either the olefin polymer of the nuclear substituted alkyl group. Such $BF_3$ phenolate catalyzed phenol alkylation with a propene polymer does not involve such molecular weight degradation. Thus by the choice of a propene polymer of carbon content equal to $C_{50}$ up to $C_{160}$ or by the choice of a higher carbon content polybutene guided by the teachings in said British Patent Specification, the desired $C_{50}$ to $C_{160}$ alkyl-substituted phenol reactant can be obtained from such $BF_3$ phenolate catalyzed alkylation process.

The substantially straight chain or alpha-olefine having the $C_{50}$ to $C_{160}$ carbon content and their resulting alkyl-substituents like the propene polymers and their resulting alkyl-substituents do not undergo the molecular weight degradation by the $BF_3$ phenolate catalysis. Hence such alpha olefins of $C_{50}$ – $C_{160}$ carbon content are auitable for the preparation of the alkylphenol reactants.

2. Phosphosulfurized Hydrocarbon

Representative of the phosphosulfurized reactants are those obtained by the reaction of a mono-olefinic hydrocarbon having from 50 up to 160 carbon atoms in its molecule with a phosphorus sulfide, such as $P_2S_3$, $P_2S_5$, $P_4S_7$, etc. and preferably $P_2S_5$. The preparation of such phosphosulfurized hydrocarbons from mono-olefinic hydrocarbons has been long known from the disclosure in U.S. Pat. No. 2,316,078 granted Apr. 6, 1943. According to said patent the mono-olefinic hydrocarbon is reacted at a temperature of from 93° C up to 230° C with $P_2S_5$ in an amount of from 1.0 up to 50, preferably 5 to 25, weight percent of the hydrocarbon reactant in a non-oxidizing (e.g. nitrogen) atmosphere and under anhydrous conditions. For the purposes of the present inventive use of the phosphosulfurized hydrocarbon it is prepared from such reaction using from 1.1 up to 1.25 moles of $P_2S_5$ for each two moles of the $C_{50}$ to $C_{160}$ mono-olefinic hydrocarbon, preferably a propylene or butylene polymer of from 700 up to 2240 $\overline{M}_n$ which has the comparable number average carbon content of from 50 up to 160 carbon atoms. Such 1.1–1.25 to 2.0 mole ratio of $P_2S_5$ to mono-olefinic hydrocarbon provides an excess, about 10 to 25% excess, of $P_2S_5$ but does provide for substantially complete reaction of the hydrocarbon. Since $P_2S_5$ is a solid, the excess thereof remaining unreacted can be removed from the liquid phosphosulfurized hydrocarbon product by filtration or by dilution with a $C_6$ to $C_{10}$ alkane, filtration of the diluted product followed by removal of the alkane diluent by distillation.

Propene and butene polymers of a least 500 $\overline{M}_n$ are preferred as the source of mono-olefinic hydrocarbon for both the preparation of the $P_2S_5$ derived phosphosulfurized hydrocarbon and the alkylphenol reactant. Such propene and butylene polymers are commercially available products. Typical of such propene and butylene products are those listed and characterized below in TABLE I.

TABLE I

| PROPENE AND BUTYLENE POLYMERS | | | |
|---|---|---|---|
| Polymer Type | $\overline{M}_n$ | Viscosity, centistokes | |
| | | 37.5° C | 98.5° C |
| Propene Polymer | 800 | 2350 | 60 |
| Propene Polymer | 975 | 5400 | 100 |
| Propene Polymer | 1120 | 14,500 | 175 |
| Butylene Polymer | 730 | 3340 | 112 |
| Butylene Polymer | 900 | 7760 | 210 |
| Butylene Polymer | 1100 | 30,000 | 642 |
| Butylene Polymer | 2200 | 145,000 | 3300 |
| Butylene Polymer | 2600 | 170,000 | 4013 |

The 2600 $\overline{M}_n$ butylene polymer is not of use as a source for the phosphosulfurized hydrocarbon. However, such 2600 $\overline{M}_n$ polymer can be used in the $BF_3$ phenolate catalysis for preparing the higher (e.g. 2000–2240 $\overline{M}_n$) alkyl-substituted phenol because of the aforementioned molecular weight degradation caused by the catalyst during alkylation. The alkyl-substituted phenol reactant having alkyl-substituents of from 700 up to 1900 can be prepared from the other butylene polymers as well as the propene polymers.

3. The Alkylene Polyamine Reactant

Representative of this class of reactants are those having two terminal primary amino groups separated by at least one alkylene hydrocarbon radical. For example, in the formula $H_2N—(ANH)_nH$ wherein $n$ is an integer from 1 to 10 and A is a saturated divalent hydrocarbon radical which contains from 0.2 to 10 carbon atoms. Thus the radical A can be from the dimethylene (ethylene) up to the decamethylene radicals inclusive as straight chain entities. However, the $C_3$ to $C_{10}$ alkylene hydrocarbon radicals can also be branched-chain as in 1,2-propylene; 1,1-dimethyl ethylene; 1-methyl propylene; the trimethyl pentylenes; etc. branched alkylenes. Such alkylene polyamines are commercially available from the reaction of $n + 1$ moles of ammonia with $n$ moles of a single or mixed alkylene dichloride. The 1,4-bis(aminoalkyl) piperazines, wherein the alkyl radical is ethyl or propyl, is a special subclass of alkylene polyamines although prepared in a different manner. Such bis(aminoalkyl) piperazines have the characteristics of the other alkylene polyamines, that is two terminal primary amino radicals ($—NH_2$) and has its amino nitrogens separated by divalent alkylene groups even in the piperazine ring. Thus the bis(aminoalkyl) piperazines are typical alkylene polyamines. Of such alkylene polyamines class of reactants they are preferred, because of their greater availability as commercial products the ethylene to decamethylene diamines, the di- to deca-ethylene and propylene (i.e., 1,2-propylene) tri-to undecamines, bid-(aminoethyl) piperazine and bis(aminopropyl) piperazine.

4. The Formaldehyde Reactant

This class of reactants includes formaldehyde per se as a gas, formalin (a 37% solution of formaldehyde in water) and paraformaldehyde. The latter two are readily recognized as commonly useful sources of formaldehyde for its reaction in situ and can be used per se. Paraformaldehyde can also be used externally by heating it externally to generate formaldehyde gas for introduction of the gas into the reaction mixture. Exemplification of the Inventive Addition Agents and Their Preparation

PREPARATION A: PHOSPHOSULFURIZED HYDROCARBON

A quantity of this reactant is prepared by reacting for 5 hours at a temperature of 232° C a mixture which has sufficient 900 $\overline{M}_n$ butylene polymer to react completely with 222 grams (1.0 mole) $P_2S_5$ under a nitrogen atmosphere. The resulting reaction of the product is the phosphosulfurized hydrocarbon. The product is analyzed to determine its phosphorus content on a weight percent basis. One mole of such product is the amount thereof containing 31 grams (1.0 gram atom) of phosphorus.

PREPARATION B: MANNICH REACTION PRODUCT

This product, when used hereafter as a reactant, is the product of 1788 $\overline{M}_n$ alkylphenol (alkyl-substituent of 1965 $\overline{M}_n$ from butylene polymer), tetraethylene pentamine and formaldehyde reacted in the respective molar proportions of 1.0:2.0:2.2 in diluent oil to provide a 50 weight percent solution of the condensation product after removal of by-product water.

EXAMPLE 1

There are combined in a stirred reaction vessel 0.3 gram mole of the Mannich Reaction product of Preparation B, 0.5 gram mole of the phosphosulfurized hydrocarbon (2.68% P) and 300 grams of SAE-5W oil. The resulting mixture is stirred, heated to a temperature of 160° C and maintained within the temperature range of 160° to 163° F for 3.5 hours while venting hydrogen sulfide. The resulting solution contains 54 weight percent of the present inventive addition agent wherein there are present for each mole of the 1788 $\overline{M}_n$ alkylphenol, 1.66 mole of the phosphosulfurized hydrocarbon, 2.0 mole of tetraethylene pentamine and 2.0 mole of formaldehyde.

EXAMPLE 2

The preparation of the present inventive addition agent is repeated according to Example 1 except that the molar ratio of phosphosulfurized hydrocarbon of Preparation A to Mannich Reaction product in oil solution of Preparation B is 1.0:1.0. The resulting oil solution is of the addition agent having the four reactants in the molar proportions of 1.0 mole of phosphosulfurized hydrocarbon (from 900 $\overline{M}_n$ butene polymer), 1.0 mole of 1788 $\overline{M}_n$ alkylphenol, 2.0 moles of tetraethylene pentamine, and 2.0 moles of formaldehyde.

EXAMPLE 3

There are charged to a stirred reaction vessel 970 grams of SAE-5W oil and 970 grams of phosphosulfurized hydrocarbon (2.84% P) derived from $P_2S_5$ and 900 $\overline{M}_n$ butylene polymer. The mixture is stirred to dissolve the phosphosulfurized hydrocarbon. Thereafter 189 grams of each of SAE-5W oil and tetraethylene pentamine (TEPA) are added to the stirred oil solution. The resulting mixture (2318 grams) is stirred and heated to 160° C and maintained at 160° C for 3 hours while venting hydrogen sulfide. The resulting product contains 1.08 mole of TEPA per gram atom of phosphorus. To a second stirred reaction vessel there is charged 1090 grams of 45.1 weight percent 1788 $\overline{M}_n$ alkylphenol (alkyl group of 1695 $\overline{M}_n$ from butylene polymer) dissolved in SAE-5W oil to provide 0.25 mole of such alkylphenol. This solution of alkylphenol is stirred while there is added 572 grams of the hot reaction product of TEPA and phosphosulfurized hydrocarbon to provide 0.25 gram atoms of phosphorus of the phosphosulfurized hydrocarbon and 0.27 mole of TEPA. Thereafter, while the mixture is stirred, 45 ml. of formalin (37% $CH_2O$) are added to provide 0.5 mole of formaldehyde. Such mixture is further diluted with an additional 273 grams of SAE-5W oil to provide an ultimate 40 weight percent of the present inventive addition agent. This stirred mixture is heated to 160° C and held at 160° C for 3 hours while injecting nitrogen gas into the solution to aid in the removal of by-product water. The addition agent so prepared as solute in lubricant oil is from the molar proportions of 1.0 mole phosphosulfurized hydrocarbon, 1.0 mole of alkylphenol, 1.08 mole of tetraethylene pentamine and 2.0 moles of formaldehyde.

EXAMPLE 4

To a stirred reaction vessel there are added 447 grams (0.25 mole) of 1788 $\overline{M}_n$ alkylphenol dissolved in 546 grams of SAE-5W oil (45% alkylphenol), an additional 200 grams of SAE-5W oil, 94.5 grams (0.5 mole) tetraethylene pentamine, and 289 grams of phosphosulfurized hydrocarbon (from $P_2S_5$ and 900 $\overline{M}_n$ butylene polymer) to provide 0.25 gram atom of phosphorus. This mixture is stirred and heated to 80° C and then 44 grams of formalin (37% $CH_2O$) are added slowly to provide 0.55 mole $CH_2O$. After all the formalin had been added, the stirred mixture is heated to 160° C and held at 160° C for 3 hours while injecting nitrogen gas into the stirred liquid to aid in the removal of by-product water and residual $H_2S$. The final solution contains 40 weight percent of the present inventive addition agent in SAE-5W oil.

EXAMPLE 5

There are combined and stirred 1790 grams of oil (SAE-5W) solution containing 50 weight percent (0.5 mole) of 1788 $\overline{M}_n$ alkylphenol, 189 grams (1.0 mole) tetraethylene pentamine, an additional 490 grams of SAE-5W oil and 200 grams (0.14 mole) of phosphosulfurized (900 $\overline{M}_n$ butylene polymer). This mixture is stirred and heated to 77° C and then 176 grams of formalin (37% $CH_2O$) are added slowly. Said mixture is stirred and heated to 160° C and maintained at 160° C for 4 hours while injecting nitrogen gas into the solution to aid in removal of water and $H_2S$ by-products. The resulting mixture is cooled to 93° C and thereafter 1210 grams (0.86 mole) additional phosphosulfurized hydrocarbon is added to the stirred solution. Such solution is then stirred at 93°–95° C for an additional 3 hours while injecting nitrogen gas into the solution to aid in the removal of $H_2S$ by-product. The final solution contains 54 weight percent of the present inventive addition agent which has the four reactants in the molar proportions of 2.0 mole phosphosulfurized 900 $\overline{M}_n$ butylene polymer, 1.0 mole of 1788 $\overline{M}_n$ alkylphenol, 2.0 mole tetraethylene pentamine, and 4.34 mole of formaldehyde.

The following comparative Products I and II are prepared according to the teachings in U.S. Pat. No. 3,458,495. The dispersancy function of said Comparative Products will later be compared against representative members of the present inventive addition agent products.

COMPARATIVE PRODUCT I

There are combined at ambient temperature in a stirred reaction vessel 550 grams of an oil solution containing one gram mole of 446 MW alkylphenol (alkyl-substituent of 352 MW corresponding to $C_{25}$, 550 grams SAE-5W oil and 30 grams (0.5 mole) ethylene diamine. Such mixture is stirred and heated to a temperature of 76.5° C and then 84 grams of formalin (36% $CH_2O$) are slowly added to provide 1.0 mole of formaldehyde. Heat is supplied to the stirred mixture to maintain it at a temperature between 82° and 88° C for 3 hours and then heated to 150° C for one hour while injecting nitrogen gas into the stirred hot liquid to aid in the removal of by-product water. The resulting oil solution contained 42.73 weight percent of the 488 M.W. Mannich Base compound from the $C_{25}$ alkyl-substituted phenol, ethylene diamine and formaldehyde used in the respective 1.0:0.5:1.0 molar ratio.

A 452 gram sample of the oil solution prepared above containing 0.396 gram mole of the Mannich Base compound is taken and transferred to a separate stirred reaction vessel. Said solution is stirred at ambient temperture while 1008 grams (1.0 mole) of phosphosulfurized butylene polymer (900 $\overline{M}_n$) containing one gram atom of phosphorus is added. The resulting stirred mixture is heated to a temperature of 205° C and maintained at said temperature while injecting nitrogen into the hot stirred liquid for 4 hours. The resulting oil solution contains 64 weight percent of the reaction product of the 1008 $\overline{M}_n$ phosphosulfurized hydrocarbon (1.0 mole $P_2S_5$ — 2 mole 900 $\overline{M}_n$ butylene polymer) and the $C_{25}$ alkylphenol derived Mannich Base compound of 488 M.W. used in the respective molar ratio of about 2.5:1.0.

COMPARATIVE PRODUCT II

There are charged at ambient temperature to a stirred reaction vessel 710 grams of SAE-5W oil and 508 grams (2.3 mole) nonylphenol. This mixture is stirred until the nonylphenol is dissolved, then 189 grams (1.0 mole) tetraethylene pentamine (TEPA) are added to the stirred solution and the resulting stirred mixture is heated to a temperature of 76.5° C. Thereafter 168 grams of formalin (36% $CH_2O$) are slowly added to provide 2.016 moles of formaldehyde. The stirred mixture is heated to and maintained at a temperature between 82° to 88° C for 3 hours and then heated to 150° C while nitrogen is injected into the hot stirred solution for one hour. The resulting oil solution contains 50.4 weight percent of the 721 M.W. Mannich Base compound from nonylphenol, TEPA and $CH_2O$ used in the respective molar ratio of 1.0:0.435:0.875.

A 300 gram sample of the foregoing oil solution containing 0.21 mole of the Mannich Base compound is taken at ambient temperature and transferred to a separated stirred reaction vessel. While said solution is stirred there are added 1010 grams (1.0 mole) of phosphosulfurized (one mole $P_2S_5$—two moles 900 $\overline{M}_n$ butylene polymer) containing one gram atom of phosphorus. The resulting mixture is heated to and maintained at a temperature of 205° C for 4 hours while nitrogen is injected into the hot stirred solution. The resulting solution contains 68 weight percent of the product of reaction between the phosphosulfurized hydrocarbon and Mannich Base compound in the respective molar ratio of 4.76:1.0.

The foregoing products of illustrative Examples 1 through 5 and Comparative Products I and II are tested for their dispersancy function according to the following test procedure.

DISPERSANCY EFFICIENCY TEST

The crankcase lubricant oil drained after extensive use in a spark ignition, internal combustion, gasoline fueled engine (e.g. crankcase lubricant oil drained from the engine following completion of the — hour Ford Sequence VC Engine Test) is used because of its content of in-service formed sludge materials which are insoluble and not dispersed in the lubricant oil, but which can be dispersed therein by an addition agent imparting the dispersancy function to the oil.

Such used (spent) crankcase lubricant oil is stirred to uniformly suspend the sludge for sampling. For the purposes of this test, there are withdrawn aliquot samples of the spent oil having suspended sludge. For any comparative series of tests, one aliquot sample is left untreated for a control basis. Each dispersant candidate for a comparative series of tests is added to separate aliquot of spent oil. The amount of dispersant candidate added is two weight percent of the addition agent. For example, where the addition agent is prepared in the presence of a lubricant base oil diluent (e.g. SAE-5W oil) so that the addition agent concentration is 40 weight percent, there is added to each 100 grams of such spent oil 5 grams (5 weight percent on spent oil) of the solution containing the 40 weight addition agent candidate.

Then the untreated and 2 weight percent treated aliquot samples of spent lubricant oil are stirred and heated to and maintained at a temperature of 150° C for 24 hours. Small samples of such hot treated and untreated spent oils are taken with a pipet. Ten drops of each oil are placed in previously ruled off and sample designated replicate squares on blotting paper. The blotting paper so treated is held at a temperature of 22° C for 24 hours. In each square the oil migrates outwardly taking the dispersed sludge with it, depending on the dispersant efficiency of the added candidate. Ideally, the diameter of the dark sludge spot will be the same as the developed oil spot. Such ideal condition represents a 100% dispersed sludge or dispersant efficiency. When inspection of the developed sludge and oil spots in each square indicates them to have different diameters, the average oil spot diameter ($D_o$) and the average sludge spot diameter ($D_s$) are determined from measurements. The dispersant efficiency is then the ratio of $D_s$ to $D_o$ multiplied by 100.

The results of such Dispersant Efficiency Tests using 2 weight percent of the actual reaction product between the Mannich Base compound and phosphosulfurized hydrocarbon in spent crankcase oil of Examples 1 through 5 and Comparative Products I and II together with the untreated (control) spent oil are shown as DE% in TABLE II. Also shown are the molar ratios of phosphosulfurized hydrocarbon ($P_2S_5HC$) to Mannich Base compound (MBC), its alkylphenol (AP) $\overline{M}_n$ and the $\overline{M}_n$ of the hydrocarbon (butylene polymer) component $N_nHC$) of the phosphosulfurized hydrocarbon.

TABLE II

DISPERSANT EFFICIENCY TEST-2 WT. % ADDITIVE

| Dispersant Candidate | $P_2S_5HC:MBC$ | $\overline{M}_nAP$ | $\overline{M}_nHC$ | DE% |
|---|---|---|---|---|
| Example 1 | 1.66:1.0 | 1788 | 900 | 100 |
| Example 2 | 1.0:1.0 | 1788 | 900 | 98 |
| Example 3 | 1.0:1.0 | 1788 | 900 | 98 |
| Example 4 | 1.0:1.0 | 1788 | 900 | 99 |
| Example 5 | 2.0:1.0 | 1788 | 900 | 98 |
| Comparative Product I | 2.5:1.0 | 446 | 900 | 76 |
| Comparative Product II | 4.76:1.0 | 220 | 900 | 82 |
| Control - No Additive | — | — | — | 63 |

From the data presented in TABLE II four conclusions can be drawn based on the fact that the hydrocarbon source (900 $\overline{M}_n$ butylene polymer) was the same for all the ($P_xS_5$ derived) phosphosulfurized hydrocarbon reactants used to prepare the severe dispersant candidates. From this fact, it can be concluded:

First, the present inventive addition agent represented by Examples 1 through 5 have to dispersant efficiency markedly superior to the addition agents (Comparative Products I and II) representative of U.S. Pat. No. 3,458,495.

Second, such dispersant efficiency superiority comes from the size ($\overline{M}_n$) of the alkylphenol reactant for the Mannich Base compound, hence the $\overline{M}_n$ of the alkyl-substituent of the alkylphenol reactant.

Third, for the present inventive addition agent the superior dispersant eficiency results from a $P_2S_5HC:MBC$ ratio no higher than 3.0:1.0 provided that the alkylphenol reactant for the Mannich Base compound has an alkyl-sustituent of the size in the $M_n$ range of from 700 up to 2240.

Fourth, to attain the dispersant efficiency of the present inventive addition agents starting with a Mannich Base compound derived from a $C_1 - C_{24}$ alkyl-substituted phenol would require, as the trend of data in TABLE II indicates, well over five moles of phosphosulfurized hydrocarbon per mole of such Mannich Base compound. Said molar proportions are outside the purview of th closest prior art ratio of 0.5 to 4.0:1.0.

Another test to show the fuctional superiority of the present inventive addition agent over the closest prior art addition agent is the Oxidative Oil Thickening Test. In this test, oil formulations of the following composition are prepared:

| Ingredient | Weight % |
|---|---|
| Base oil | 87.31 |
| Addition Agent Candidate | 5.0 |
| 400 TBN Magnesium Sulfonate | 1.26 |
| Ethoxylated Phenol | 0.12 |
| Polyacrylate VI Improver | 6.23 |

Such oil formulations, including the formulation with no oxidation thickening deterrent addition agent, are stirred and heated to and mainatined at a temperature of 171° C and stirred while injecting air into the hot stirred oil. The air injection is continued until the viscosity of the oil formulation is increased four fold. The number of hours to reach such 4 Vo viscosity is the basis for comparing the effectiveness of the addition agent candidate to suppress oxidative thickening of the oil.

The solution of Example 5 further diluted with SAE-5W oil to 40 weight percent of the present inventive addition agent, Comparative Products I and II, the normal calcium salt of the $P_2S_5$ phosphosulfurized 900 $\overline{M}_n$ butylene polymer (prior art use o the $P_2S_5HC$ above as additive) and a Mannich Base compound from 1.0 mole 1788 $\overline{M}_n$ alkylphenol, 1.1 mole tetraethylene pentamine and 2.0 mole of formaldehyde are all tested at 5.0 weight percent as addition agent candidates in the above described Oxidative Oil Thickening Test. The results of such tests, time to reach 4 Vo, are shown in TABLE III.

TABLE III

OXIDATIVE OIL THICKENING TEST to 4 Vo

| Candidate | Time to 4 Vo, hours |
|---|---|
| None-Control | 15 |
| Calcium $P_2S_5HC$ | 60 |
| Mannich Base | 34 |
| Example 5 | 75 |
| Comparative Product I | 28 |
| Comparative Product II | 38 |

From the data in TABLE III, it is seen that the Mannich Base (intermediate component of the present inventive addition agent) has little beneficial effect against oxidative oil thickening and the calcium salt of $P_2SHC$ is somewhat more effective against oxidative oil thickening. However, the effectiveness of comparative products I and II are not better than the Mannich Base and are inferior to the calcium salt. But the Example 5 product representative of the present inventive addition agent is again markedly superior not only to its components but also and more important to the closest prior art products. Such superiority is, it is submitted, the result of chemically combining the $P_2S_5HC$ and Mannich Base components of the present invention.

To illustrate the effectiveness of the present inventive addition agent as a component of automatic transmission lubricant composition the following oil formulation was prepared:

| Ingredient | Volume % |
|---|---|
| SAE-5W oil | 88.5 |
| Polyacrylate VI improver | 3.5 |
| Solution of Example 4 | 7.0 |
| Anti-Corrosion Agent * | 0.3 |
| Anti-Foam Agent | 0.7 |

* A 2,5-bis(octyl dithio)-1,3,4-thiadiozde

The test procedure is the well known Dexron II automatic transmission lubricant oil test conducted for 250 hours after which the quality of the oil is evaluated, the transmission parts are inspected for cleanliness and the condition of the O-ring oil seals are evaluated for distortion and swelling. The results from the use of the above oil formulation are:

| | |
|---|---|
| Oil Quality | Good |
| Transmission Cleanliness | Essentially Clean |
| Seals | Not distorted or swollen |

Having described, exemplified and demonstrated the practice and utility of the present invention to enable those skilled in this art to understand the same and practice and use the present invention, its scope is defined by the claims which follow.

The invention claimed is:

1. A product obtained by the condensation of a (1) $C_{50}$ to $C_{160}$ alkyl-substituted phenol, (2) an alkylene polyamine, (3) a source of formaldehyde, and (4) a phosphosulfurized hydrocarbon derived from $P_2S_5$ and a 500 up to 2240 $\overline{M}_n$ olefin polymer used in the respective molar reactant proportions of the four reactants of 1.0:0.1–10.0:1.0–10.0:0.5–3.0.

2. The product of claim 1 wherein the condensation is conducted in the presence of a diluent which is a petroleum fraction of the lubricant oil range corresponding to SAE-5W up to SAE-30 viscosity oils.

3. The product of claim 2 wherein reactants (1), (2) and (3) are first condensed in the presence of SAE-5W oil as a diluent under conditions removing by-product water to form a first intermediate and such intermediate is then reacted with the phosphosulfurized hydrocarbon.

4. The product of claim 2 wherein reactants (4) and (2) are combined in the oil diluent and heated to a temperature of 160° C and thereafter reactants (1) and (3) are reacted with the product of reactants (4) and (2) at a temperature of 160° C until all by-products are removed.

5. The product of claim 2 wherein reactants (1), (2) and (4) are combined in the lubricant oil diluent and heated to a temperature in the range of 70° up to 80° C, then reactant (3) is added and the resulting mixture is heated to a temperature of from 90° up to 180° C until all by-products have been removed.

6. The product of claim 5 wherein reactant (1) is a 1788 $\overline{M}_n$ alkylphenol, reactant (2) is tetraethylene pentamine, reactant (3) is formalin, and reactant (4) is the product of reacting one mole of $P_2S_5$ with two moles of 900 $\overline{M}_n$ butylene polymer; and the amount of oil diluent used provides a 10 to 50 weight percent of the condensation product of reactants (1), (2), (3), and (4).

* * * * *

UNITED STATES PATENT OFFICE
CERTIFICATE OF CORRECTION

Patent No. 4,031,017            Dated June 21, 1977

Inventor(s) ALBERT R. SABOL

It is certified that error appears in the above-identified patent and that said Letters Patent are hereby corrected as shown below:

Col. 2, line 66, "Mn" should read --$\overline{\text{Mn}}$--

Col. 3, line 10, "prepared,The" should read --prepared. The--

Col. 3, line 37, "reaction. the" should read --reaction.The--

Col. 3, line 41, "produect" should read --product--

Col. 4, line 42 "condtions" should read --conditions--

Col. 7, line 4 "bid-" should read --bis---

Col. 7, line 36, "1965 $\overline{\text{Mn}}$" should read --1695 $\overline{\text{Mn}}$--

Col. 10, line 34, "unformly" should read --uniformly--

UNITED STATES PATENT OFFICE
CERTIFICATE OF CORRECTION

Patent No. 4,031,017  Dated June 21, 1977

Inventor(s) ALBERT R. SABOL

It is certified that error appears in the above-identified patent and that said Letters Patent are hereby corrected as shown below:
(CONT'd)

Col. 11, lines 10-11 "component $N_nHC$) of" should read --component $(MnHC)$ of--.

Signed and Sealed this

First Day of November 1977

[SEAL]

Attest:

RUTH C. MASON  
*Attesting Officer*

LUTRELLE F. PARKER  
*Acting Commissioner of Patents and Trademarks*